United States Patent [19]

Seidman et al.

[11] Patent Number: 4,465,521
[45] Date of Patent: Aug. 14, 1984

[54] DIACETONE FRUCTOSE HYDROLYSIS WITH WATER-INSOLUBLE CATALYSTS

[75] Inventors: Martin Seidman, Decatur; Carl W. Niekamp, Forsyth, both of Ill.

[73] Assignee: A. E. Staley Manufacturing Company, Decatur, Ill.

[21] Appl. No.: 445,113

[22] Filed: Nov. 29, 1982

[51] Int. Cl.$^3$ .................. C13D 1/00; C13K 11/00
[52] U.S. Cl. .................. 127/36; 127/46.2; 536/4.1; 536/18.6; 536/124; 536/127
[58] Field of Search .................. 127/36, 46.1, 42, 53, 127/46.2; 536/4.1, 128, 127, 18.6, 124

[56] References Cited

U.S. PATENT DOCUMENTS

| | | | |
|---|---|---|---|
| 2,715,121 | 8/1955 | Glen et al. | 536/4.1 X |
| 2,813,810 | 11/1957 | Smith et al. | 127/55 |
| 2,857,374 | 10/1958 | Baird | 536/124 X |
| 3,607,862 | 9/1971 | Jaffe et al. | 536/124 |
| 3,622,560 | 11/1971 | Hindley et al. | 536/124 |

OTHER PUBLICATIONS

Studies of Glycosides and Isopropylidene Derivatives—K. Erne Acta Chemica Scandinavica 9, 1955, pp. 893–901.
Acid-Catalyzed Hydrolysis of Isopropylidene Acetals of Some 2-Pentuloses and 2-Hexuloses—Tipson et al.—Carbohydrate Research 10, 1969, pp. 181–183.

*Primary Examiner*—Kenneth M. Schor
*Attorney, Agent, or Firm*—Forrest L. Collins; Philip L. Bateman; M. Paul Hendrickson

[57] ABSTRACT

Diacetone fructose solutions may be effectively hydrolyzed to fructose by acid exchange resins. Hydrolysis of diacetone fructose with acid exchange resins substantially reduces the formation of objectionable flavoring, coloring and other hydrolyzate by-products. The immobilized acid catalysis provides a fructose product substantially free from ash residues and significantly reduces the carbon, cation and anion exchange requirements for the manufacture of enriched, food-grade fructose syrups. Perfluorinated acid exchange resins have been found to be particularly effective for hydrolyzing aqueous diacetone fructose solutions into fructose.

9 Claims, No Drawings

DIACETONE FRUCTOSE HYDROLYSIS WITH WATER-INSOLUBLE CATALYSTS

BACKGROUND OF THE INVENTION

U.S. Pat. No. 2,813,810 by Smith et al. discloses a method for fractionating invert sugar into glucose and fructose. In the Smith et al. method, the fructose of invert sugar is converted to diacetone fructose by acid catalysis with a commercial sulfonated phenol-formaldehyde ion exchange resin. After separating the dextrose precipitate and resin, the concentrated alpha-diisopropylidene D-fructose supernatant solution was hydrolyzed with 0.01N sulfuric acid at an elevated temperature for 12 hours. The hydrolyzate was neutralized by passing the syrup through an anion exchange resin. Crystalline fructose was recovered by dissolving the hydrolyzed concentrate in hot absolute ethanol and its crystallization therefrom by cooling.

In a paper authored by K. Erne ("Studies of Glycosides and Isopropylidene Derivatives" *Acta Chemica Scandinavica* 9, (1955), pages 893–901), acetone and fructose were catalyzed into 1,2-4,5-diisopropylidene D-fructopyranose. Erne observed that fructose readily converted into a brown, degradation product upon exposure to acid catalysts. Tipson et al. ("Acid-catalyzed hydrolysis of isopropylidene acetals of some 2-pentuloses and 2-hexuloses" *Carbohydrate Research* 10 (1969) pages 181–183) later reported that the acid-catalyzed hydrolysis of diacetone fructose with strong mineral acids (e.g. hydrochloric and sulfuric acids as disclosed by Erne, Smith et al. and others) produced high levels of decompositional by-products of fructose. Tipson et al. found that catalysis with 100 mM oxalic acid for 1–2 hours at 65° C. would substantially reduce the level of fructose degradation.

Fructose may be obtained from a variety of natural and synthetic sources. High fructose corn syrups (HFCS) are conventionally manufactured by enzymatically isomerizing high dextrose conversion syrups. The enzymatic isomerization of dextrose syrups can provide fructose syrups which compositionally contain from about 30%–52% fructose, 40%–54% dextrose, 1%–4% disaccharide and from about 3%–8% saccharides of a $D.P._3$ or higher. Since fructose is sweeter than dextrose, it is conventional to enrich the fructose content of a HFCS (e.g. 55%–90% or higher) by chromatographic fractionation and separation techniques. Food-grade syrups must necessarily be essentially free from organoleptically detectable by-products, which are often detectable in trace amounts. The elution of the fractionated monosaccharides under conventional enrichment processes leads to substantial dilution of the eluted products with water. Substantial capital equipment investments, evaporating, recycling, quality control and other manufacturing expenses are incurred under conventional fructose enrichment processes. It would be desirable to manufacture food-grade, 55%+HFCS syrups by a technique other than chromatographic fractionation and separation.

The laboratory studies of Erne, Smith et al. and Tipson et al. cannot be effectively applied to the fructose enrichment of HFCS. Many food applications for the enriched HFCS necessitate that the product be free from objectionable and organoleptically detectable flavor, color and other degradative by-products. Tipson et al. recognized substantial degradation of fructose arose as a result of the mineral acid hydrolyzing conditions of Smith et al. and Erne. Tipson et al. proposed to alleviate this problem by replacing the hydrolyzing mineral acids with a toxic acid (oxalic acid) which would be unacceptable for the manufacture of food products.

The acetonation of fructose is generally capable of yielding two isomeric forms of diacetone fructose. In modern practice, these isomers are generally referred to as 1,2:4,5 di-O-isopropylidene beta-D-fructopyranose and 2,3:4,5 di-O-isopropylidene beta-D-fructopyranose. The 1,2:4,5 isomer is generally prepared under kinetically controlled conditions whereas the thermally stable 2,3:4,5 form will generally require higher temperatures, higher concentrations of acid catalyst and longer reaction periods.

Within recent years, perfluorinated exchange resins with functionally active acid (e.g. sulfonic and/or carboxylic groups) have gained prominence for a variety of industrial applications. The commercially available perfluorinated ionic membranes are reportedly produced by a variety of chemical processes as disclosed in *C&EN*, Mar. 15, 1982 "Electrolytic cell membrane development surges" by S. C. Stinson, pages 22–25.

DESCRIPTION OF THE INVENTION

According to the present invention there is provided a method for hydrolyzing diacetone fructose into fructose. The method comprises contacting an aqueous diacetone fructose solution with a catalytically effective amount of cationic exchange materail to hydrolyze the diacetone fructose to fructose, hydrolyzing the diacetone fructose to fructose and recovering the fructose.

Pursuant to the present invention, aqueous diacetone fructose solutions may be directly hydrolyzed with an acid exchange resin into fructose. The exchange resin functions as an acid catalyst. The water-insoluble, acid exchange resins more effectively hydrolyze the diacetone fructose into fructose while avoiding catalytic or other objectionable by-product contamination of the enriched fructose product. Such exchange resins typically comprise a water-insoluble, polymeric matrix and functionally active acidic groups immobilized or affixed to the polymer matrix. A variety of commercially available ion exchange resins may be used for this purpose. Illustrative polymeric matrices for such ion exchange resins include copolymers comprised of a major proportion of styrene copolymerized with a minor proportion of divinylbenzene, phenol-formaldehyde condensates, epoxy-polyamine resins, perfluorinated resins and other polymeric matrices of lesser commercial significance. Compositionally, the acid radicals will generally be comprised of oxygen and at least one other atom selected from the group consisting of a Period II element of an atomic weight range of about 10 to about 14 (e.g. boron, carbon, nitrogen) and Period III element of an atomic weight ranging from about 28 to about 32 (e.g. phosphorous, sulfur, etc.). Illustrative acid groups chemically affixed to commercially available polymeric matrices include sulfonic, carboxylic, phosphonic, phosphonous, phosphoric, etc. acid groups. The strong acid catalyst, such as the sulfonic acid are especially effective exchange resin catalysts. Macroreticular, gelular, granular, beads, sheets, fragmented membranes and other solid forms of the acid exchange resins may be used as hydrolyzing catalysts.

The perfluorinated cation exchange resins have been found to be particularly effective catalysts for hydrolyzing aqueous diacetone fructose solutions to fructose.

These resins are typically comprised of a perfluorinated polymeric backbone chain which contains a plurality of appendant acid groups. Illustratively perfluorinated exchange resins may be generally depicted by the polymeric structural formula: $+[(CF_2CF_2)_n-C_2F_3Q]_x$ wherein "Q" represents an appendant acid group, "n" is an integer representing the number of tetrafluoroethylene units which intervene between the Q-containing trifluoroethylene units and "x" the number of polymeric acid groups. The appendant Q groups are typically comprised of a perfluorinated ionic moiety represented by the formula: $-Q'-A^+$, wherein Q' represents a perfluorinated linking group and $A^+$ an acid group. The Q' group will typically consist essentially of a perfluoro-organo moiety connected to the polymeric carbon atom via an oxy or difluoromethylene radical which forms a bridging linkage between the polymeric chain and the ionic moiety. The commercially available exchange resins reportedly contain, as a Q' group, either the $+(CF_2)_{2-5}-$ and/or $-O-CF_2-CF(CF_3)-O(CF_2)_{1-5}-$ linking moiety. The appendant groups will typically contain either phosphorous, carbon and/or sulfur-containing organic acid groups. The perfluorinated strong acid resin (particularly the perfluorinated sulfonic acid exchange resins) are especially effective and potent catalysts for hydrolyzing diacetone fructose into fructose.

The hydrolysis is conducted with a sufficient amount of acid exchange resin to catalytically convert the diacetone fructose to fructose. This amount can vary considerably and will depend largely upon the hydrolyzing efficacy of the particular exchange resin. The weak cation exchange resins (e.g. carboxylic and carboxylated resins) generally require a higher catalyst concentration than the intermediate acid types such as the phosphonic, phosphorous, phosphoric acids and salts. Exchange resins of sulfonic acids and the salts thereof are classified as strong cation exchange resins and may be used at considerably lower catalytic levels than the intermediate acid resins. The perfluorinated ionic catalysts are particularly potent acid catalysts. They may be utilized in the hydrolysis of diacetone fructose to fructose at substantially lower temperatures and catalytic concentrations. Enriched fructose products which use the perfluorinated acid catalysts to hydrolyze the diacetone fructose to fructose herein have been found to be essentially free from organoleptically and other objectionable (e.g. color, flavor, degradative, etc.) bodies. The electron attracting fluorine atoms of the perfluorinated resins increases the catalytic activity of the acid site by about a 5-6 fold factor in comparison to the non-fluorinated exchange resins. Although relatively small amounts of catalyst (e.g. 1 meq. fructose mole or less) to levels in excess of 1000 meq. or higher may be used for this purpose, a catalyst level of about 2 meq. to about 800 meq. will normally be sufficient to hydrolyze the diacetone fructose to fructose. Advantageously the amount of catalyst will range from about 5 meq. to about 700 meq. with the preferred catalytic usage level ranging from about 10 meq. to about 400 meq. For the perfluorosulfonic acid resin it is advantageous to use less than 20 meq. in the hydrolysis.

Advantageously, the acid exchange resin will be provided in a form which is easily separable from the hydrolyzate products. If desired, the reactor and/or stirring equipment may be coated with the perfluorinated exchange resin to provide the catalytic source for the hydrolysis. Alternatively, a sheet, granular, fragmented membrane, beads, etc. of a dimensional size sufficient to permit ease of separation may be used as the hydrolyzing catalyst. The catalytic reaction may be adapted to batch, semi-continuous and continuous reactor systems. The nature and character of the perfluorinated exchange catalysts herein render it ideally suited for a continuous operation. In such an operation, the aqueous diacetone fructose solution may be continuously fed or passed through a single or plurality of fixed beds containing the immobilized perfluorosulfonated resin, or reactors impregnated or coated therewith. The solution flow rate and reaction temperature may be suitably monitored to optimize conversion of diacetone fructose to fructose.

The catalytic hydrolysis of diacetone fructose to fructose is a reversible reaction. The hydrolysis reaction is generally favored by providing a sufficient amount of water to the hydrolyzing medium to shift the equilibrium towards fructose production. Catalytic reconversion of the fructose and acetone into diacetone fructose will generally be inhibited by maintaining the molar ratio of water to total acetone (free and chemically combined) during the hydrolysis reaction at a level in excess of about 11:10 and advantageously at a level of more than about 2:1 moles water for each mole acetone. Further excesses of water (e.g. 30 moles or higher) may be used but are generally unnecessary and undesirable due to additional processing and equipment needed to remove excess water and place the recovered fructose in a marketable form. In a commercial operation, more effective and complete hydrolysis of the diacetone fructose will be obtained by generally maintaining the water level at least about 3 moles and preferably in excess of 10 moles for each acetone mole. During the hydrolysis, the free acetone is advantageously removed from the hydrolyzing medium (e.g. evaporating under a vacuum) as it is formed by the hydrolyzing reaction. Removal of the free acetone during the hydrolysis will further facilitate more complete hydrolysis of the diacetone fructose into fructose.

In the manufacture of enriched fructose syrups of a 55% or higher fructose content, the hydrolyzing medium will more typically contain about 2 moles to about 50 moles water per fructose mole and advantageouslu from about 5 moles to about 30 moles water for each fructose mole. If desired, the water content of the reaction product may be adjusted to more closely approximate that of the desired syrup end-product. By maintaining the free acetone level during the hydrolysis at less than about 2 moles acetone (preferably less than 1 mole) for each five moles water, substantially complete catalytic conversion of the diacetone fructose into fructose may be accomplished.

Diacetone fructose is generally prepared by the acetonation of fructose with acid catalyst and molar excesses of acetone. The conversion of a fructose containing syrup into diacetone fructose with an acid catalyst is most suitably conducted under conditions which favor the production of the 1,2:4,5 di-O-isopropylidene beta-D-fructopyranose. This will provide a substrate which may be readily hydrolyzed with the catalytic resin into fructose. The acetonation is most suitably conducted at a temperature of less than 35° C. to produce a diacetone fructose solution substantially free from the 2,3:4,5 di-O-isopropylidene-beta-D-fructopyranose isomer. A variety of fructose-containing syrups may be utilized as a fructose source for the acetonation. Fructose-containing products obtained through enzymatic modification of sugars (particularly the isomerization of dextrose syrups with glucose isomerase) are suitable sources for the fructose. Although fructose syrups of about 30% to about 55% may be suitably adapted to acetonation, commercially available fructose containing corn syrups of about 38%-46% fructose content (d.s.b.) are especially well suited for adaptation to this invention. The strong acid exchange resins mentioned above are particularly effective catalysts for the acetonation of fructose into 1,2:4,5-diisopropylidene D-beta-fructopyranose. Upon completion of the diacetone fructose reaction, the dextrose is allowed to precipitate from the diacetone solution. Upon completion of the dextrose precipitation the resultant diacetone fructose solution will, on a total dry solids weight basis, contain a substantially higher diacetone fructose content.

An enriched fructose syrup may be appropriately recovered from diacetone fructose solutions (e.g. such as obtained by the acetonation of 38%-46% HFCS) by removing a sufficient amount of unreacted acetone to permit the acid hydrolysis thereof and its conversion into fructose. The hydrolysis of diacetone fructose to fructose will yield two moles of acetone for each fructose mole. If insufficient water is present during the hydrolysis, acetone may be removed or additonal water added to complete the hydrolysis. The acetone generated by the hydrolysis reaction may be removed during the hydrolysis to insure more complete conversion of the diacetone fructose to the desired fructose product. In a commercial operation, it is advantageous to remove sufficient acetone (e.g. evaportion, distillation, etc.) to provide a hydrolyzing medium which contains molar excesses of water. Preferably, substantially all of the excess acetone is removed from the diacetone fructose solution prior to its hydrolysis with the exchange resins.

The reaction temperature and time intervals are suitably regulated so as to convert 1,2:4,5-diisopropylidene-D-fructopyranose into fructose. The most appropriate temperature and contact time depend to a large extent upon the type of reactor and catalyst. In a continuous operation, more elevated temperatures may be used provided reaction time is shortened sufficiently to avoid excessive decomposition of the fructose. The contact time interval in a continuous process may be appropriately controlled by regulating the flow rate of reactants through the reactor. Longer reaction periods may be effectively used in batch or continuous reactors by reducing the reaction temperture. Although relatively high hydrolyzing temperatures (e.g. 80° C. or higher) may be used for enriched fructose production in which by-products are unimportant, a decided advantage herein is the ability to employ lower than normal (e.g. less than 70° C.) hydrolyzing temperatures. A hydrolyzing temperature of less than about 65° C. (e.g. about 20° C. to about 65° C.) and especially less than about 60° C. (preferably about 50° C. to about 60° C.) can be effectively used to convert the diacetone fructose into fructose. By reducing the thermal requirements for the catalytic conversion reaction, unexpectedly superior reductions in fructose degradative products are achieved.

Upon completion of the diacetone hydrolysis, the immobilized catalyst (if present) may be removed from the hydrolyzed solution, the hydrolyzate adjusted (if necessary) with an appropriate acid to about pH 3 to about pH 5 (preferably from about pH 3 to about pH 4) and any acetone residue removed from the hydrolyzate by conventional techniques such as by distillation, evaporation, etc. Pursuant to the present process, syrups of an enriched fructose content of at least 55% (e.g. 55%-90% or higher fructose content) and preferably of a fructose content of about 60% to about 90% may be easily prepared from 38%-46% HFCS. Notwithstanding the high fructose content, the acid hydrolysis produces an enriched fructose syrup products substantially free from objectionable flavoring and coloring bodies. This substantially reduces the carbon, cationic and anionic exchanged resin requirements for placing these syrups in a marketable condition for food applications. The immobilized catalysts provide syrups essentially free from ash residues which normally arise from salts formed by neutralizing water soluble catalyst with a base.

The following examples are illustrative of the invention.

EXAMPLE 1

This example illustrates the use of a perfluorinated sulfonic acid resin[1] to prepare a 75% fructose syrup from 40.4% HFCS[2]. The reactants were prepared by adding 900 ml. of acetone to 68.2 grams of 40.4% high fructose syrup. The reactants and solid catalyst (112 square inches of the perfluoronated sulfonic acid membrane—14 meq.) were stirred at 24°-25° C. for 45 hours. Under these acetonation conditions, the fructose was converted to 1,2:4,5-di-O-isopropylidene-beta-D-fructopyranose with a substantial portion of the dextrose being precipitated from the liquid solution. The membrane was then removed and the dextrose precipitate was filtered (Whatman No. 2paper) from the single liquid phase. Saccharide analysis by high pressure liquid chromatography (HPLC) of the unwashed precipitate revealed that the precipitate consisted of 74.3% dextrose, 18.6% fructose and a balance (7.1%) primarily of $D.P._2$ and higher sugars. Analysis of the liquid phase by HPLC indicated it contained 24.0% dextrose, 29.9% fructose, 44.7% diacetone fructose (86.4% by weight being 1,2:4,5-di-O-isopropylidene-beta-D-fructopyranose) and the balance (1.4%) being comprised of $D.P._2$ and higher saccharides. Substantially all of the unreacted acetone was then removed from the liquid phase by aspirating with water vacuum in a rotary evaporator in a 60° C. water bath for about 20 minutes. The evaporated syrup (28% solids) was then heated to 65° C. for 2 hours in the presence of 6.3 sq. in. of the perfluorinated sulfonic acid catalyst (0.8 meq.) to hydrolyze the diacetone fructose to fructose. The acetone generated by the hydrolysis was continuously removed by the above rotary evaporating conditions to provide a 50% by weight dry solids syrup product. Analysis of the hydrolyzed product by high pressure liquid chromatography indicated it contained 74.3% fructose and 22.5% dextrose with the balance (3.2%) being primarily comprised of di- and higher HFCS saccharide components.

[1]—Nafion 125—A copolymer of tetrachloroethylene perfluoro-3,6-dioxa-4-methyl-7-octensulfonic acid membrane manufactured and distributed by E. I. du Pont de Nemours & Co., Wilmington, Del. 19898
[2]—40.4% fructose, 55.3% dextrose, 2.6% maltose and isomaltose and 1.7% by weight saccharide of $D.P._3$ and higher.

The unrefined, enriched fructose syrup (23.2 grams), which contained 50% by weight dry solids, was blended with sufficient 40% high fructose corn syrup[2] (50% d.s.) to provide an enriched fructose syrup containing 55% by weight (d.s.b.) fructose content. The blended 55% high fructose corn syrup (pH 3.5) was then treated with powdered carbon (3% by weight of 55% HFCS dry solids weight) for 30 minutes at 60° C. and filtered through Whatman No. 2 filter paper. The carbon-treated filtrate was then ion exchanged (40° C.) through a pair of cation and anion exchange columns. The syrup effluent of a dry substance in excess of 20% by weight solids was collected, adjusted to a pH 3.5, and concentrated under aspirating vacuum (water) in a rotary evaporator immersed in a 60° C. water bath to a 78% dry solids syrup. When evaluated by an expert syrup flavor panel, the 55% high fructose corn syrup received an average flavor grade rating of 8.5±0.5 (1–10 basis). The syrup was characterized as being as colorless, bland, sweet-tasting syrup essentially free from other flavor principles. This flavor rating exceeded those typically obtained from conventional 55% HFCS.

EXAMPLE 2

Example 1 was repeated by replacing the perfluorinated sulfonic acid catalyst with another acid ion exchange resin. The acetonation reaction was conducted by mixing 100 grams (d.s.) of the styrene/divinylbenzene sulfonic acid exchange resin (Dowex 50WX1-100 (50–100 mesh)) with 1187 acetone and 694 grams high fructose corn syrup for 21 hours at 26° C. and an additional 22 hours at 18° C. The decrease in catalytic temperature to 18° C. was designed to optimize the rate of dextrose precipitation from the diacetone fructose solution. The dextrose precipitate was separated by filtrating (Whatman No. 2 filter paper) at 18° C. The catalytic resin was removed by sieving through a 200 mesh screen (U.S. Series), washed with water and the washings combined with the liquid diacetone fructose filtrate. The acetone was evaporated from the filtrate by aspirating with a rotary evaporator maintained at 40° C. The HPLC analysis of the dextrose precipitate for saccharide revealed that the dextrose precipitate contained 91.2% dextrose, 7.2% fructose and 1.6% D.P.$_2$ and higher saccharides. An HPLC analysis of the filtrate revealed (on a total dry solids weight basis) 10.7% diacetone fructose, 35.0% dextrose and 44.9% fructose. The level of fructose by-products was higher than that obtained for the perfluorinated sulfonic acid membrane used for the acetonation.

In the regeneration of the diacetone fructose to fructose, 650 ml. of the concentrated filtrate syrup (34% dry solids) was treated with 3 grams (dry substance basis) Dowex 50WX4-200 for 3 hours at 45°–85° C. After the catalyst was separated by filtration, the acetone generated by the diacetone fructose hydrolysis was removed from the filtrate (as described hereinbefore) to provide a 46.5% dry substance fructose syrup which, upon HPLC analysis, revealed a saccharide distribution (on a total dry substance weight basis) of 57.8% fructose, 35.8% dextrose and 6.4% D.P.$_2$ and higher saccharides.

Complete hydrolysis with the perfluorinated sulfonic acid resin of Example 1 can be effectuated at about 0.01–0.2 meq. H$^+$/DAF mole within about 2 hours. In contrast, diacetone fructose hydrolysis with the styrene/divinylbenzene acid exchange resin will typically require more catalyst (e.g. about 0.3–1.5 meq. H$^+$/mole diacetone fructose, i.e. DAF) and time (about 2–4 hours) to completely hydrolyze the diacetone fructose to fructose. The hydrolyzate of this example with the styrene/divinylbenzene acid exchange yielded a slightly discolored solution in contrast to the clear solution obtained in Example 1 with the perfluorinated sulfonic acid resin.

To further illustrate the advantages of using acid exchange resins in the conversion of diacetone fructose solutions to fructose, the diacetone fructose solution of Example 1 was completely hydrolyzed to fructose with 0.2 meq. oxalic acid/mole DAF for 4 hours at 65° C. The completely hydrolyzed diacetone fructose solution obtained through use of the oxalic acid was significantly more discolored (yellowish brown solution) than either of those prepared with the acid exchange resins. The excessive oxalic acid contamination of the hydrolyzed solution rendered it unfit for food use. In another experiment, 0.01N hydrochloric acid (0.02 meq. H$^+$/M mole/DAF) was used to hydrolyze the DAF solution of Example 1. The hydrolysis was conducted at 90° C. for 6 hours. Employing hydrochloric acid as the hydrolyzing acid, a black (indicative of excessive degradation) hydrolyzate product was obtained. Similar charred hydrolyzate results may be obtained when other strong mineral acids are employed as the hydrolyzing acid.

What is claimed is:

1. A method for converting diacetone fructose to fructose, said method comprising (a) contacting an aqueous diacetone fructose solution with a catalytically effective amount of water-insoluble perfluorinated acid exchange resin; (b) hydrolyzing a substantial portion of diacetone fructose to fructose and acetone; (c) separating the resulting solution from contact with the acid exchange resin; and (d) recovering the fructose.

2. The method according to claim 1 wherein at least a major portion of the diacetone fructose is converted to fructose.

3. The method according to claim 1 wherein the catalytically active sites of the exchange resin consist essentially of sulfonic acid.

4. The method according to claim 1 wherein the aqueous diacetone fructose solution is prepated from a high fructose corn syrup containing (on a total dry solids weight basis) about 38% to about 46% by weight fructose content.

5. The method according to claim 4 wherein acetone is removed from the hydrolyzing medium during the hydrolysis of the diacetone fructose to fructose.

6. The method according to claim 4 wherein the aqueous diacetone fructose solution contains about 5 to about 30 moles water for each fructose mole, less than 1 mole of free acetone for each 5 moles water and the hydrolyzing temperature ranges from about 50° C. to about 60° C.

7. The method according to claim 1 wherein substantially all of the diacetone fructose is hydrolyzed to fructose with a perfluorinated sulfonic acid catalyst.

8. The method according to claim 7 wherein the catalyst concentration is less than 20 meq./fructose mole.

9. The method according to claim 7 wherein a fructose syrup having a fructose content ranging from about 60% to about 90% by weight (dry solids weight basis) is recovered from the hydrolyzed diacetone fructose solution.

* * * * *